United States Patent [19]

Tsuchida et al.

[11] Patent Number: 5,338,672
[45] Date of Patent: Aug. 16, 1994

[54] METHOD FOR PRODUCING L-3, 4-DIHYDROXYPHENYLALANINE BY ERWINIA HAVING TYROSINASE ACTIVITY

[75] Inventors: Takayasu Tsuchida; Yoshitaka Nishimoto; Takuya Kotani; Katsuo Iizumi, all of Kawasaki, Japan

[73] Assignee: Ajinomoto Co., Inc., Tokyo, Japan

[21] Appl. No.: 36,268

[22] Filed: Mar. 24, 1993

[51] Int. Cl.$^5$ ............................................. C12P 13/22
[52] U.S. Cl. ................................... 435/108; 435/232; 435/847; 435/252.1
[58] Field of Search ...................... 435/108, 232, 252.1, 435/847

[56] References Cited

U.S. PATENT DOCUMENTS 3,791,924  2/1974  Ogata et al. .................... 435/108

OTHER PUBLICATIONS

Database WPIL, AN-93-199733, JP-A-5 123 177, May 21, 1993.
Database WPIL, AN-76-31196X, JP-B-51 009 394, Mar. 27, 1976.
Argicultural and Biological Chemistry, vol. 37, No. 3, 1973, pp. 493-499, H. Enei, et al., "Synthesis of L-Tyrosine or 3,4-Dihydroxyphenyl-L-Alanine From DL-Serine And Phenol Or Pyrocathechol".
Enei, H. et al., "Distribution of Tyrosine Phenol Lyase in Microorganisms", *Agr. Biol. Chem.*, vol. 36, No. 11, pp. 1861-1868, 1972.
Soda, K. et al., "Amino Acids", In. Biotechnology, vol. 3, Dellweg, H. (ed.); Publishi: Verlag Chemie: pp. 503-506, 1983.

*Primary Examiner*—Douglas W. Robinson
*Assistant Examiner*—Marian Knode
*Attorney, Agent, or Firm*—Oblon, Spivak, McClelland, Maier & Neustadt

[57] ABSTRACT

The present invention relates to improved methods for producing L-3, 4-dihydroxyphenylalanine from catechol, pyruvic acid and ammonium ion, or catechol and L-serine, by utilizing β-tyrosinase activity of a microorganism which belongs to the genus Erwinia. According to the method of the present invention, L-3,4-dihydroxyphenylalanine can be produced at a lower cost and higher efficiency as compared with that in the conventional method.

3 Claims, No Drawings

METHOD FOR PRODUCING L-3, 4-DIHYDROXYPHENYLALANINE BY ERWINIA HAVING TYROSINASE ACTIVITY

BACKGROUND OF THE INVENTION

1. Field of the Invention

This invention relates to a method for producing L-3,4 dihydroxyphenylalanine (hereinafter referred to as L-DOPA). L-DOPA is widely used as medicine for treating Parkinson disease.

2. Discussion of the Background

Conventionally, as a method for producing L-DOPA, a synthetic method which uses vanillin as the starting material has been widely known. On the other hand, various methods for producing L-DOPA by utilizing enzymatic systems of a microorganism have been studied, including a method for producing L-DOPA from catechol, pyruvic acid and ammonium ion by utilizing β-tyrosinase (Japanese Patent Publication No. 73-34237; U.S. Pat. No. 3,791,924), a method from catechol and L-serine and other amino acids by utilizing β-tyrosinase (Japanese Patent Publication No. 72-22275; U.S. Pat. No. 3,791,924), a method from dihydroxycinnamic acid and ammonium ions by utilizing ammonia-lyase (Japanese Patent Publication No. 87-24076), a method from L-phenylalanine or L-tyrosine by utilizing oxygenase (Japanese Patent Publication Nos. 72-19033 and 72-14915) and a method from 3,4-dihydroxyphenylpyruvic acid by utilizing transaminase (Japanese Patent Publication No. 83-18475).

However, the production of L-DOPA using any of these methods is costly, and there is a need for a method for producing L-DOPA which is both inexpensive and provides high efficiency.

It is an object of the present invention to provide a method for producing L-DOPA which provides lower production cost and higher efficiency as compared with conventionally known methods for producing L-DOPA, by improving a method for producing L-DOPA which utilizes the β-tyrosinase of a microorganism.

As the result of the present research, to improve a method for producing L-DOPA, which utilizes the β-tyrosinase of a microorganism, we have found that the productivity of L-DOPA is largely improved by modifying the preparation method of the culture containing β-tyrosinase, the source of ammonium ion and/or the way of adding the substrates in the reaction mixture. Based on the obtained results, we have completed the present invention.

SUMMARY OF THE INVENTION

That is, the present invention provides a method for producing L-DOPA by contacting a culture of a microorganism belonging to the genus Erwinia and having β-tyrosinase activity, cells recovered from the culture, or a product obtained by processing the recovered cells, with catechol, pyruvic acid and ammonium ion, or catechol and L-serine, wherein said method utilizes the culture obtained by further incubating the culture for 6 to 24 hours after the growth of the cells reaches the stationary Phase, with the pH of the culture being maintained within a range of between 7 and 8.3, the cells recovered from said culture, or the product obtained by processing the recovered cells.

Also the present invention provides for a method for producing L-DOPA by contacting a culture of a microorganism belonging to the genus Erwinia and having β-tyrosinase activity, cells recovered from the culture, or a product obtained by processing the recovered cells, with catechol, pyruvic acid and ammonium ion, wherein said method uses ammonium chloride as the source of ammonium ion in the reaction mixture.

Additionally, the present invention provides for a method for producing L-DOPA by contacting a culture of a microorganism belonging to the genus Erwinia and having β-tyrosinase activity, cells recovered from the culture, or a product obtained by processing the recovered cells, with catechol, pyruvic acid and ammonium ion, or catechol and L-serine, wherein a solution of catechol is continuously or intermittently added into the reaction mixture so that the concentration of catechol is maintained at 1.0% wt. or lower.

DETAILED DESCRIPTION OF THE PREFERRED EMBODIMENTS

The microorganism used in the present invention can be any strain which belongs to the genus Erwinia and has β-tyrosinase activity (tyrosine phenol-lyase; EC.4.1.99.2) and specifically, as examples, the following strains can be used:

*Erwinia herbicola* ATCC 21433
*Erwinia herbicola* ATCC 21434

Additionally, a microorganism which is derived from any of these strains and whose L-DOPA productivity is improved by using techniques such as mutation treatment and genetic engineering can be used in the present invention.

Concerning the preparation of a culture of any of these microorganisms, the strain is grown in a medium containing carbon sources, nitrogen sources, minerals, and other nutrients. As the carbon sources, substances including glycerol, fuanaric acid, and saccharides are appropriately used; as the nitrogen sources, substances including ammonium sulfate and amino acids are used; and as the minerals, substances including potassium phosphate, magnesium sulfate, iron(II) sulfate, manganese sulfate, and zinc sulfate are appropriately used; and as other nutrients, substances such as yeast extract, peptone, soybean protein hydrolysate, and amino acids are used. Since β-tyrosinase appears to be an inducible enzyme, β-tyrosinase activity is increased, and therefore a preferable result can be obtained, by the addition of tyrosine or a tyrosine equivalent into the medium. It is also effective to add substances belonging to the vitamin $B_6$ group into the medium for increasing β-tyrosinase activity.

Concerning conditions of cultivation, it is proper to perform the cultivation at a temperature of between 15° and 45° C. As to the pH of the medium and the period for cultivation, in the conventional method, as disclosed in U.S. Pat. No. 3,791,924, the cultivation was to be performed for 10 to 72 hours while the pH being adjusted to 5.5 to 8.5, but in the present method, the culture is further incubated for 6 to 24 hours while the pH being maintained at between 7.0 and 8.3, after the growth of the cells reaches the stationary phase.

The stationary phase is reached, during the batch process for culturing cells, after the logarithmic or exponential growth phases. At the stationary phase, the cell population has reached its maximum size.

According to the present method, β-tyrosinase activity per unit volume of the culture thus obtained is more than twice as high as that obtained by the conventional methods, and thus a culture which is more suitable for L-DOPA production can be obtained. That is, the present method can significantly shorten the reaction time and achieve higher reaction yields during the reaction process. The reason why β-tyrosinase activity obtained by the conventional methods remains at a lower levels is that, it has not been known that further incubation of the culture under careful pH control after the growth of the cells reaches the stationary phase has a significant effect on the level of β-tyrosinase activity, as described in the present invention.

As the source of β-tyrosinase in the reaction, the thus obtained culture which is not subjected to any further process, cells recovered from the culture by means of centrifugation, filtration, etc, or a product obtained by processing the cells, such as disrupted cells, acetone-treated cells, immobilized cells, cell extract or purified β-tyrosinase obtained from the cell extract can be used.

Next, concerning the reaction process to obtain L-DOPA by contacting the culture of a microorganism belonging to the genus Erwinia and having β-tyrosinase activity, the cells recovered from the culture, or the product obtained by processing the recovered cells, with catechol, pyruvic acid and ammonium ion, special attention has not been paid to the type of source of ammonium ion in the conventional methods and any ammonium salt including ammonium acetate, ammonium chloride, ammonium sulfate ammonium nitrate, ammonium phosphate and ammonium salts of any organic acid, was believed to be used equally as the source of ammonium ion. However, it is amazing to find that when ammonium chloride is used as the source of ammonium ion, the production rate for L-DOPA is more than twice as fast as that in the reaction using other ammonium salts. That is, L-DOPA can be produced with higher efficiency by using ammonium chloride as the source of ammonium ion.

In addition, concerning the reaction process to obtain L-DOPA by contacting the culture of a microorganism belonging to the genus Erwinia and having β-tyrosinase activity, the cells recovered from the culture, or the product obtained by processing the recovered cells, with the substrates catechol, pyruvic acid and ammonium ion, conventionally, catechol, pyruvic acid and ammonium ion were to be added into the reaction mixture in the whole quantity at the beginning of the reaction or in divided portions during the reaction.

However, the production rate and accumulation of L-DOPA are significantly improved compared to those by the conventional addition method in the present method in which a solution of catechol (added with substances including pyruvic acid and ammonium ion or other if necessary) is added continuously or intermittently into the reaction mixture so that the concentration of catechol is maintained at 1.0% wt. or lower. That is, in the conventionally known procedure of divided addition of catechol in the crystal form, denaturation and inactivation of β-tyrosinase in the reaction mixture caused by the addition of catechol could not be prevented enough and as the result, accumulation of L-DOPA remains at a lower level. On the other hand, according to the procedure for adding catechol in the present invention, L-DOPA can be produced from catechol, pyruvic acid and ammonium ion at a significant efficiency and a high accumulation.

Also, in the method to produce L-DOPA by contacting the culture of a microorganism belonging to the genus Erwinia and having β-tyrosinase activity, the cells recovered from the culture, or the product obtained by processing the recovered cells, with catechol and L-serine, it is also effective to prevent inactivation of β-tyrosinase by continuously or intermittently adding a solution containing catechol (added with L-serine or other substances, if necessary) into the reaction mixture so that the concentration of catechol is maintained at 1.0% wt. or lower, and according to this method, L-DOPA can be also efficiently produced.

If desired, reducing agents including sodium sulfite and cystseine, and chelating agents including EDTA and citric acid may be added into the reaction mixture. The proper reaction temperature is between 10° and 60° C., the proper pH is between 7.7 and 8.7, and the reaction period is to be appropriately determined according to the activity and concentration of β-tyrosinase used for the reaction and the concentration of the substrates.

After the reaction is completed, L-DOPA produced in the reaction mixture can be recovered by means of the standard isolation and purification procedures including steps of concentration and treatment using ion-exchange resins. Such as those disclosed in U.S. Pat. No. 3,791,924.

Having generally described this invention, a further understanding can be obtained by reference to certain specific examples which are provided herein for purposes of illustration only and are not intended to be limiting unless otherwise specified.

EXAMPLE 1

A loopful of cells of *Erwinia herbicola* ATCC 21433, which had been prepared by the 24-hour incubation at 31.5° C. on a bouillon agar medium, was inoculated into 500 ml-flasks with 50 ml of the seed cultivation medium having the composition of Table 1, and the cultivation was performed by shaking at 31° C. for 12 hours. Then 30 ml each of the culture thus prepared was inoculated into 500 ml-jar fermentere with 300 ml of the main cultivation medium having the composition of Table 2, and cultivation was initiated at 28° C.

TABLE 1

| Components | Concentrations (% wt.) |
|---|---|
| Glycerol | 1 |
| KH$_2$P0$_4$ | 0.05 |
| MgSO$_4$ · 7H$_2$O | 0.05 |
| FeSO$_4$ · 7H$_2$O | 0.001 |
| ZnSO$_4$ · 7H$_2$O | 0.001 |
| Fumaric acid | 0.2 |
| L-tyrosine | 0.2 |
| Soy protein hydrolysate | 1.5 |
| Pyridoxine | 0.01 |
| pH 7.5 (KOH) | |

TABLE 2

| Components | Concentrations (% wt.) |
|---|---|
| Glycerol | 0.5 |
| KH$_2$PO$_4$ | 0.05 |
| MgSO$_4$ · 7H$_2$O | 0.05 |
| FeSO$_4$ · 7H$_2$O | 0.001 |
| ZnSO$_4$ · 7H$_2$O | 0.001 |
| Fumaric acid | 0.7 |
| L-tyrosine | 0.2 |
| Glycine | 0.3 |
| DL-alanine | 0.3 |
| DL-methionine | 0.1 |
| L-phenylalanine | 0.2 |
| L-sodium glutamate | 0.55 |
| Soy protein hydrolysate | 1.0 |
| Pyridoxine | 0.01 |
| Defoaming agent | 0.002 |

TABLE 2-continued

| Components | Concentrations (% wt.) |
|---|---|
| pH 7.5 (KOH) | |

The cultivation was then continued, while the pH of the culture was maintained at 7.5 by the addition of potassium hydroxide and glucose, and the growth of the cells reached the stationary phase approximately 24 hours after the initiation of the cultivation. From this point, the pH of the culture tended to slowly increase, so the pH was maintained at 6.5, 7.0, 7.5, 8.0, 8.3, and 8.5 respectively by the addition of acetic acid, and the culture was further incubated for another 24 hours (total incubation time was 48 hours). The cells were recovered by means of centrifugation from 10 mL of each culture obtained after 24, 30 and 48 hours after the initiation of cultivation, and each recovered cells were added to 10 mL of the reaction mixture having a composition of Table 3. The reaction mixture was allowed to react at room temperature for one hour, and then the $\beta$-tyrosinase activity of the cells in a unit culture volume was measured.

TABLE 3

| Components | Concentrations (% wt.) |
|---|---|
| Sodium pyruvate | 2.0 |
| Catechol | 1.0 |
| Ammonium chloride | 2.0 |
| Ammonium nitrate | 0.1 |
| Sodium sulfite | 0.2 |
| EDTA | 0.2 |
| pH 8.0 (aqueous ammonia) | |

As the result, $\beta$-tyrosinase activity in the culture obtained by, after the growth of the cells reached to the stationary phase, further incubating the ells for 6 to 24 hours while the pH of the culture was maintained between 7.0 and 8.3, was significantly higher as shown in Table 4.

TABLE 4

| | L-DOPA production activity (g/dl/hr) | | |
|---|---|---|---|
| pH | 24 hours | 30 hours | 48 hours |
| 6.5 | 0.5 | 0.3 | 0.3 |
| 7.0 | 0.5 | 0.6 | 0.9 |
| 7.5 | 0.5 | 0.9 | 1.3 |
| 8.0 | 0.5 | 1.0 | 1.5 |
| 8.3 | 0.5 | 0.8 | 1.3 |
| 8.5 | 0.5 | 0.4 | 0.4 |

EXAMPLE 2

Cultivation of *Erwinia herbicola* ATCC 21433 was performed according to the same method as described in Example 1. After the 24-hour incubation, that is, at the point when the growth of the cells reached the stationary phase, the culture was further incubated for 12 hours while the pH of the culture was maintained at 7.5 by addition of acetic acid (total cultivation period was 36 hours). Then the cells were recovered from 10 mL of the culture by means of centrifugation and added to the same amount of each of reaction mixtures having the composition of Table 5 which contained the source of ammonium ion selected from substances consisting of ammonium acetate, ammonium chloride, ammonium sulfate and ammonium phosphate, and $\beta$-tyrosinase activity of each reaction mixture was determined according to the same method described in Example 1. In this Example, the concentration of ammonium ion in each reaction mixture was 0.4M.

TABLE 5

| Components | Concentrations (% wt.) |
|---|---|
| Sodium pyruvate | 2.0 |
| Catechol | 1.0 |
| Ammonium ion | 0.4 M |
| Ammonium nitrate | 0.1 |
| Sodium sulfite | 0.2 |
| EDTA | 0.2 |
| pH 8.0 (aqueous ammonia) | |

As the result, when ammonium chloride was used as the source of ammonium ion, $\beta$-tyrosinase activity was more than twice as high as that obtained using other sources of ammonium ion, as shown in Table 6.

TABLE 6

| Sources of ammonium ion | L-DOPA production activity (g/dl/hr) |
|---|---|
| Ammonium acetate | 0.4 |
| Ammonium chloride | 1.3 |
| Ammonium sulfate | 0.5 |
| Ammonium nitrate | 0.3 |
| Ammonium phosphate | 0.3 |

EXAMPLE 3

Cultivation of *Erwinia herbicola* ATCC 21433 was performed according to the same method as described in Example 1. After 24-hour incubation, that is, at the point when the growth of the cells reached the stationary phase, the culture was further incubated for 12 hours while the pH of the culture was maintained at 7.5 by addition of acetic acid (Total cultivation period was 36 hours). Then the cells were recovered from 225 mL of the culture by means of centrifugation, and added with 225 mL of reaction mixtures having the composition of Table 7 to initiate the reaction at 15° C. During the reaction, the mixture was periodically sampled as time passed, and a solution containing each 20% wt. of catechol and sodium pyruvate was continuously added to the mixture so that the concentration of remaining catechol in each reaction mixture was kept at 0.5% wt. or lower, 1.0% wt. or lower, or 1.5% wt. or lower. The amount of L-DOPA produced during the 16--hour reaction was 10.0 g/dl, 9.0 g/dl and 5.0 g/dl, respectively. Separately, for the purpose of comparison, a reaction was also performed by adding catechol and sodium pyruvate in the form of crystals several times during the reaction so that the concentration of the remaining catechol was kept at 1.0% wt. or lower, and as the result, 3.0 g/dl of L-DOPA was accumulated in the reaction mixture.

TABLE 5

| Components | Concentrations (% wt.) |
|---|---|
| Sodium pyruvate | 1.5% |
| Catechol | 1.0% |
| Ammonium chloride | 4.0% |
| Ammonium nitrate | 0.1% |
| Sodium sulfite | 0.2% |
| EDTA | 0.3% |
| pH 8.0 (aqueous ammonia) | |

Next, 100 ml of the mixture which completed reaction and contained 10.0 g/dl of L-DOPA was acidified to dissolve crystals of L-DOPA, and the cells were removed by means of centrifugation. Obtained supernatant was concentrated to 45 ml and poured into a column of active carbon, then adsorbed L-DOPA was eluted with dilute aqueous ammonia containing 0.2% wt. of sodium sulfite. Fraction containing L-DOPA was concentrated, and the obtained residue was dissolved with hydrochloric acid, neutralized, then again concentrated to obtain crude crystal of L-DOPA. Recrystallization was repeated three times to obtain 5.2 g of purified crystal of L-DOPA.

EXAMPLE 4

By using cells of *Erwinia herbicola* ATCC 21433 prepared according to the same method described in Example 3, the reaction was performed at 15° C for 18 hours in the reaction mixture having the composition of Table 8, while an aqueous solution containing each 20% wt. of catechol and L-serine continuously added to the reaction mixture so that the concentration of catechol in the mixture was maintained at 0.5% wt. or lower. As a result, after the reaction was completed, 10.2 g/dl of L-DOPA was accumulated in the mixture. A total of 4.2 g of purified crystals of L-DOPA was obtained from 100 mL of the reaction mixture according to the same method described in Example 3.

TABLE 8

| Components | Concentrations (% wt.) |
| --- | --- |
| L-serine | 1.5 |
| Catechol | 1.0 |
| Ammonium nitrate | 0.1 |
| Sodium sulfite | 0.2 |

TABLE 8-continued

| Components | Concentrations (% wt.) |
| --- | --- |
| EDTA | 0.3 |
| pH 8.0 (aqueous ammonia) | |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for producing L-3,4-dihydroxyphenylalanine, comprising:
    culturing a microorganism belonging to the species *Erwinia herbicola* and having β-tyrosinase activity until reaching a stationary phase,
    further maintaining the culture for 6 to 24 hours while maintaining the pH within a range of from 7 to 8.3,
    recovering said cells from said culture,
    contacting said cells with catechol, pyruvic acid and ammonium ion, or catechol and L-serine to produce L-3,4-dihydroxyphenylalanine, and
    recovering said L-3,4-dihydroxyphenylalanine.

2. The method of claim 1, wherein said contacting step is conducted with catechol, pyruvic acid and ammonium ion, and said ammonium ion is ammonium chloride.

3. The method of claim 1, wherein said catechol is maintained at a concentration of 1.0% by wt. or lower.

* * * * *

UNITED STATES PATENT AND TRADEMARK OFFICE
CERTIFICATE OF CORRECTION

PATENT NO. : 5,338,672

DATED : August 16, 1994

INVENTOR(S) : Takayasu TSUCHIDA et al

It is certified that error appears in the above-identified patent and that said Letters Patent is hereby corrected as shown below:

COLUMN 2, LINE 36, "fuanaric" should read --fumaric--.

COLUMN 3, LINE 26, "methods" should read --methods,--.

COLUMN 5, LINE 36, "ells" should read --cells--.

Signed and Sealed this

Seventh Day of November, 1995

*Attest:*

BRUCE LEHMAN

*Attesting Officer*  Commissioner of Patents and Trademarks